United States Patent [19]

Papa et al.

[11] 4,162,353

[45] Jul. 24, 1979

[54] METHOD OF PRODUCING FLEXIBLE FLAME RETARDED POLYURETHANE FOAM

[75] Inventors: Anthony J. Papa, Saint Albans; Walter W. Runyan, Charleston, both of W. Va.

[73] Assignee: Union Carbide Corporation, New York, N.Y.

[21] Appl. No.: 892,752

[22] Filed: Apr. 3, 1978

Related U.S. Application Data

[62] Division of Ser. No. 644,789, Dec. 29, 1975, Pat. No. 4,097,559.

[51] Int. Cl.$^2$ ............................................... C08K 5/52
[52] U.S. Cl. ................................................... 521/107
[58] Field of Search .................... 260/2.5 AJ; 521/107

[56] References Cited

U.S. PATENT DOCUMENTS

| 3,896,187 | 7/1975 | Weil | 521/107 |
| 3,959,415 | 5/1976 | Shim et al. | 521/107 |

*Primary Examiner*—Veronica P. Hoke
*Attorney, Agent, or Firm*—Dale Lynn Carlson

[57] ABSTRACT

Novel haloalkyl polyphosphates are prepared by reacting at elevated temperatures a halosubstituted alkyl phosphate such as, for example, tris (2-chloroethyl) phosphate, and an unsubstituted trialkyl phosphate such as, for example, triethyl phosphate. The character of the mixture of the thermal condensates formed can be influenced by the ratio of reactants employed and the extent to which the reaction is allowed to proceed. The resulting reaction products possess superior flame retardant efficiency and impart durable flame resistance when incorporated into flexible urethane foams.

10 Claims, No Drawings

METHOD OF PRODUCING FLEXIBLE FLAME RETARDED POLYURETHANE FOAM

This application is a division of our prior U.S. application Ser. No. 644,789, filed Dec. 29, 1975, now U.S. Pat. No. 4,097,559.

BACKGROUND OF THE INVENTION

This invention relates to polyurethanes and, more particularly, to novel haloalkyl polyphosphates capable of imparting long term, flame retardant durability to such polyurethanes.

Considerable effort has been made to provide polyurethane foams with satisfactory flame retardancy. In general, a wide variety of organophosphorus compounds, typically containing chlorine and/or bromine, have been proposed and utilized. These compounds are conventionally designated as being of either the additive type or the active type. The latter type possess functionality which allows chemical incorporation into the resulting polyurethane.

The problem of providing adequate flame retardancy is particularly acute when flexible urethane foams are involved. It is thus generally accepted that achievement of adequate flame retardant durability in flexible urethane foams at acceptable levels of the flame retardant (i.e. - the ability to maintain an adequate level of flame retardancy after exposure to heat aging conditions) requires utilizing flame retardants of the reactive type.

For example, two of the commercially used material of the additive type have the following structural formulas:

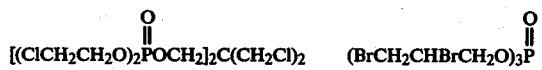

$$[(ClCH_2CH_2O)_2POCH_2]_2C(CH_2Cl)_2 \qquad (BrCH_2CHBrCH_2O)_3P$$

1　　　　　　　　　　　　2

These impart durability but achieve this only by use of relatively high levels. In addition to the associated economic penalty, relatively high levels of flame retardants often adversely affect certain physical properties of the foams such as, for example, tensile and tear strength and compression sets.

A further approach utilizes flame retardant materials which are described as haloethylterminated phosphoric acid ester polymers having repeating phosphate ester groups interconnected with ethylene ester groups. These compounds are formed by heating a tris (2-haloethyl) phosphate or a mixture of 2-haloethyl phosphoric acid ester compounds containing at least 50% by weight of tris (2-haloethyl) phosphate and up to 50% by weight of at least one other phosphoric acid ester having at least one 2-haloethyl substituent to a temperature within the range of 170° C. to 220° C. in the presence of a basic catalyst for a period of time sufficient to generate reaction by-product ethylene dihalide in an amount of from 0.5 mole to 0.9 mole per mole of the 2-haloethyl phosphorous reactant.

In use, such compounds have been principally employed as flame retardants for textiles. No substantial acceptance in polyurethane foam formulations have been achieved. Such compounds are typically insoluble in various conventional polyols used in flexible foams, and this lack of compatibility can cause inconsistent flame retardant and foam properties, particularly when introduced with a stream including the polyol. In addition, such compounds require relatively high levels to achieve adequate flame retardant durability.

It is accordingly an object of the present invention to provide novel organophosphates capable of imparting improved flame retardancy to polyurethanes. A related and more specific object lies in the provision of novel organophosphates which impart improved flame retardancy to flexible polyurethane foams.

A further object provides flame retardants which impart, in terms of flame retardance, long term durability for flexible polyurethane foams.

Yet another object of this invention is to provide novel organophosphates having superior compatibility with flexible polyurethane foam formulations. A more specific and related object provides organophosphates which are soluble in polyols typically used for forming flexible urethane foams.

Yet another object provides novel organophosphates which may be economically manufactured.

Another object lies in the provision of organophosphates characterized by relatively high flame retardant efficiency.

Other objects and advantages of the present invention will become apparent from the following detailed description.

SUMMARY OF THE INVENTION

The present invention, in general, provides novel haloalkyl polyphosphates which comprise the reaction product of a halosubstituted alkyl phosphate and an unsubstituted trialkyl phosphate. The liquid residue product comprises a mixture of the thermal condensates of the reactants and is capable of imparting outstanding durable flame resistance when incorporated into flexible urethane foams in relatively minor amounts (i.e. - possesses superior flame retardant efficiency).

DETAILED DESCRIPTION OF THE INVENTION AND PREFERRED EMBODIMENTS

With respect to the haloalkyl substituted phosphate reactant, this must possess at least one chloro or bromoalkyl chain connected to the phosphorous through an oxygen atom. Conceptually, any reactant may be used which is capable of entering into a cyclic, concerted intramolecular displacement reaction in which the O nucleophile attacks the C atom of the chain bearing the halo group, which in turn attacks the C atom of the O-alkyl-phosphorous ester, thereby converting the P-O-alkyl linked groups to P=O. Visually, this reaction may be generally characterized as follows:

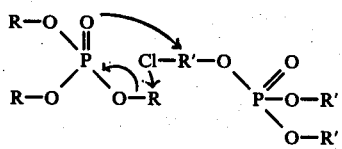

When a 2-haloalkyl phosphate is employed, the composite structural formula is as follows:

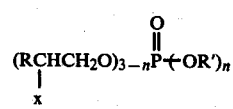

wherein n=0, 1, or 2 and x=Cl or Br. Illustrative species are provided when R is H, CH₃, CH₂Cl or CH₂Br and R' is methyl, ethyl, propyl or butyl.

Specific examples of commercially available species include:

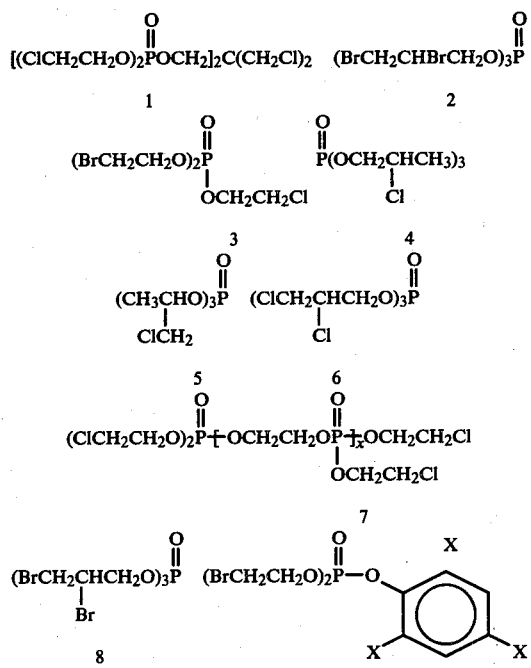

Still further species which may be useful include:

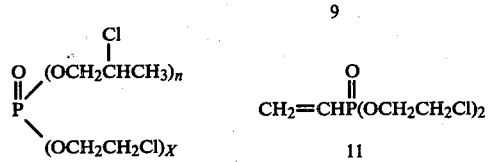

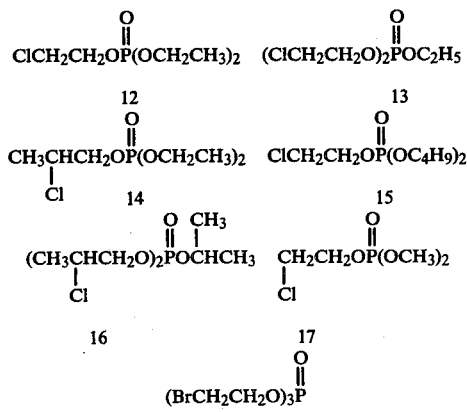

The specie selected may well be dictated by economics. For this reason, symmetrical halosubstituted phosphates may generally prove particularly useful. However, a material comprising a mixture of the compounds identified as 4 and 5 is commercially available and could be ecomonically employed. In addition, the bromo species will provide a more facile reaction: and the dihalosubstituted species will, of course, provide a somewhat higher halogen content in the resulting polymer product.

With respect to the unsubstituted trialkylphosphate reactant, any organophosphate containing at least one low molecular weight alkyloxy group connected to the phosphorous atom should be useful. A generalized structural formula for this reactant is shown below:

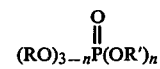

wherein R is $CH_3$, $C_2H_5$, $C_3H_7$, or $C_4H_9$: R' is $C_5$ to $C_{10}$ hydrocarbon chains and n is 0, 1, or 2. The utilization of an organophosphate in which at least one low molecular weight alkyloxy group is connected to the phosphorous atom insures that the reaction proceeds simply and efficiently. Due to ease in making the starting reactant, it may be preferred to employ a symmetrical trialkyl phosphate.

Mixtures of one or both of the reactants may be used if desired.

The novel organophosphates of the present invention may be readily obtained by heating a mixture of the halosubstituted phosphate and the unsubstituted trialkyl phosphate at elevated temperatures for the time needed to carry the thermal condansation to the desired extent. The process of this invention may be tailored to provide a wide variance of type of reaction products. The particular type of reaction products desired may be achieved by proper coordination of the various process parameters involved such as temperature, reaction time, reactant species selected, reactant ratio and catalyst type (when used).

A catalyst need not be employed but may be useful to influence parameters such as the reaction time and temperature needed to achieve a particular stage of condensation as well as the color of the resulting product. These aspects will be discussed in greater detail hereinafter.

Useful catalysts include bases and Lewis acid salts. Suitable basic catalysts include alkali metal and alkaline earth metals, such as sodium, magnesium, calcium; their oxides, hydroxides, carbonates, bicarbonates, alkoxides (e.g.—sodium ethoxide), phenolates and salts of strong bases and weak acids such as alkali metal and alkaline earth metal acetates, and phosphates, and salts of organic phosphorus acids and partial phosphate esters. Organic bases such as amines, for example, pyridine, quinoline, triethylamine, tetramethylguanidine, N-methylmorpholine, butylamine and aniline may be used. Lewis bases are also contemplated.

With respect to acidic catalysts, a variety of cation and anion combinations may be utilized. Suitable cations include lithuim, sodium, cesium, potassium, magnesium, lead, and the like while suitable anions include dimethylamine, chloride, fluoride, nitrate, sulfate and the like.

The reaction temperatures utilized may vary from about 120° C. to 200° C. or higher. The minimum temperature required is, of course, that which is needed to initiate and sustain the desired thermal condensation while the upper limit is generally dictated by safety considerations. The use of appropriate catalysts will tend to lower somewhat the useful temperatures. In general, temperatures in the range of from about 165° C. to about 180° C. are preferred.

The reaction time employed will typically vary from about 1 to about 5 hours or more, depending upon the other process parameters used. A longer reaction time may well result in some thermal degradation occurring; and, in this connection, use of a catalyst will generally reduce the reaction time needed.

The ratios of the phosphate reactants may be varied within wide limits; however, the reaction will be limited by the amount of the halosubstituted reactant which is present. Also, as will be described hereinafter in connection with the products formed, the ratio employed will also influence the type of product formed.

The facile nature of the process of this invention will also be effected by the nature of the byproducts formed. More specifically, to facilitate the reaction, it is desirable to select reactants such that the halide evolved from the reaction has a boiling point below that of the dihalide formed. Thus, for example, when tris (2-haloethyl) phosphate is utilized, the halide species formed are desirably $C_1$-$C_4$ halides.

The extent of the reaction may be controlled solely by selecting a particular reaction time or by control of other process parameters. Thus, if desired, control may be achieved by appropriate monitoring of the viscosity. Viscosities of the reaction product may range from, for example, about 300 cps. (25° C.) or so to about 17,000 or more. The character of the reaction product formed varies accordingly. Typically, as will be discussed in greater detail hereinafter, higher viscosities will indicate a higher extent of branching. Similarly, monitoring the amount of byproduct dihalide being formed can provide a useful indication. In this instance, it will generally be desirable to continue the reaction until anywhere from about 0.35 to about 0.45 moles or so of the dihalide is collected per mole of the halosubstituted reactant. The reaction may be stopped short of the indicated range, if desired; however, the average molecular weight of the reaction product will tend to be lower than generally useful. Higher values will usually not be obtained unless the unsubstituted phosphate is present in somewhat less than a stoichiometric amount.

It will generally be desirable to neutralize the reaction product so as to reduce the acid number to an acceptable level. This may be carried out by any conventional means, and treatment with epichlorohydrin has been found to provide the product with satisfactorily low acid numbers. Further known refining techniques, such as stripping and the like, may be carried out if desired.

The resulting reaction product comprises a mixture of thermal condensates and is a liquid with a color varying from black to colorless. In this connection, the use of an appropriate catalyst will tend to allow production of colorless liquids. The product viscosity varies over a wide range as previously described, and products at the lower end are soluble in polyols conventionally used in flexible foam formulations while increasing viscosities tend to make the product less compatible. Products with viscosities at the high end of the range have been found to be insoluble in such polyols.

To achieve all of the advantages of the present invention, it is generally preferred to provide a reaction product which is compatible with the polyols used. However, in some applications, compatibility may not be necessary.

The reaction products may, in general, be characterized by the following repeating units;

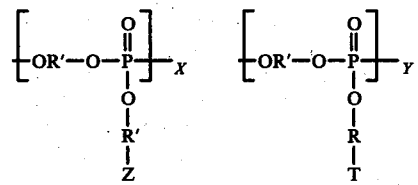

wherein R is the alkyl moiety of the unsubstituted trialkyl phosphate, R' is a hydrocarbon moiety of the halosubstituted phosphate reactant,

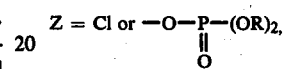

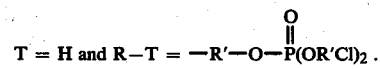

The integral value of X and Y will, of course, be determined by the extent of the reaction which takes place. As should be appreciated, when

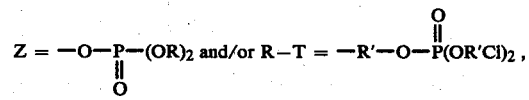

further condensation can take place. The character of the polymer backbone can be tailored by appropriate selection of the halosubstituted phosphate since alkyl groups of the unsubstituted trialkyl phosphate reactant can be present only at the ends of the polymer chain. The first three molecules which react (at least one necessarily being the halosubstituted phosphate) will form the initial backbone of the growing chain. In the case where equimolar amounts of the reactants are present, likely structures include:

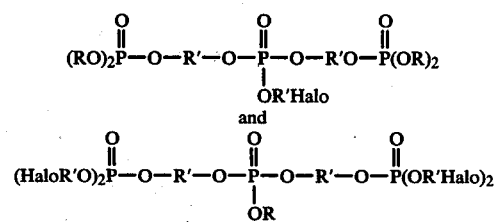

Further reaction will favor chain extension rather than branching. If the trialkyl phosphate is present in excess (e.g.—a molar ratio of 3/1), a likely structure will be:

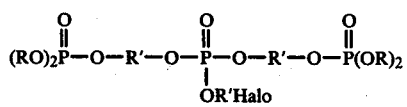

Further reaction will favor branching rather than chain extension.

As can accordingly be appreciated, the selection of the reactant ratio will influence whether the resulting reaction product polymers are generally linear or are highly branched. To achieve more linear polymers, it will be desirable to employ a reactant ratio of the unsubstituted trialkyl phosphate to the halosubstituted phosphate of from about 1:1 to 2:1. Increasing ratios will generally provide more highly branched structures.

It is also believed that the viscosity of the reaction product reflects the character of the polymer chain. Thus, after a certain point, continued condensation will tend towards more branching, with concomitant higher viscosities. Control of the extent of condensation by monitoring the viscosity will provide a means to allow formation of reaction products having the desired polymer structure.

The flexible polyurethane foams with which the novel haloalkyl polyphosphates of the present invention may be utilized may be prepared by reacting and foaming: (a) a polyol, (b) an organic polyisocyanate, (c) a catalyst for the reaction of (a) and (b) to produce the polyurethane, (d) a blowing agent and (e) a foam stabilizer. The reaction and foaming operations can be performed in any suitable manner, preferably by the one-shot technique.

The polyols which may be employed can be a polyhydroxyalkane, a polyoxyalkylene polyol, or the like. Among the polyols which can be employed are one or more polyols from the following classes of compositions, alone or in admixture, known to those skilled in the polyurethane art:

(a) Alkylene oxide adducts of polyhydroxyalkanes;
(b) Alkylene oxide adducts of non-reducing sugars and sugar derivatives;
(c) Alkylene oxide adducts of phosphorus and polyphosphorus acids;
(d) Alkylene oxide adducts thereof of polyphenols;
(e) The polyols from natural oils such as castor oil, and the like.

Illustrative alkylene oxide adducts of polyhydroxyalkanes include, among others, the alkylene oxide adducts of ethylene glycol, propylene glycol, 1, 3-dihydroxypropane, 1, 3-dihydroxybutane, 1, 4-dihydroxybutane, 1, 4-, 1, 5- and 1, 6-dihydroxyhexane, 1, 2-, 1, 3-, 1, 4-, 1, 6-, and 1, 8-dihydroxyoctane, 1, 10-dihydroxydecane, glycerol, 1, 2, 4-trihydroxybutane, 1, 2, 6-trihydroxyhexane, 1, 1, 1-trimethylolethane, 1, 1, 1-trimethylolpropane, pentaerythritol, caprolactone, polycaprolactone, xylitol, arabitol, sorbitol, mannitol, and the like; preferably the adducts of ethylene oxide, propylene oxide, epoxybutane, or mixtures thereof. A preferred class of alkylene oxide adducts of polyhydroxyalkanes are the ethylene oxide, propylene oxide, butylene oxide, or mixtures thereof, adducts of trihydroxyalkanes.

A further class of polyols which can be employed are the alkylene oxide adducts of the non-reducing sugars, wherein the alkylene oxides have from 2 to 4 carbon atoms. Among the non-reducing sugars and sugar derivatives contemplated are sucrose, alkyl glycosides such as methyl glucoside, ethyl glucoside, and the like, glycol glycosides such as ethylene glycol glucoside, propylene glycol glucoside, glycerol glucoside, 1, 2, 6-hexanetriol glucoside, and the like, as well as the alkylene oxide adducts of the alkyl glycosides as set forth in U.S. Pat. No. 3,073,788.

As still further useful class of polyols is the polyphenols, and preferably the alkylene oxide adducts thereof wherein the alkylene oxides have from 2 to 4 carbon atoms. Among the polyphenols which are contemplated are found, for example, bisphenol A, bisphenol F, condensation products of phenol and formaldehyde, the novolac resins; condensation products of various phenolic compounds and acrolein; the simplest member of this class being the 1, 1, 3-tris (hydroxyphenyl) propanes, condensation products of various phenolic compounds and glyoxal, glutaraldehyde, and other dialdehydes, the simplest members of this class being the 1, 1, 2, 2-tetrakis (hydroxyphenol)ethanes, and the like.

The alkylene oxide adducts of phosphorus and polyphosphorus acids are another useful class of polyols. Ethylene oxide, 1, 2-epoxypropane, the epoxybutanes, 3-chloro-1, 2-epoxypropane, and the like are preferred alkylene oxides. Phosphoric acid, phosphorus acid, the polyphosphoric acids such as tripolyphosphoric acid, the polymetaphosphoric acids, and the like are desirable for use in this connection.

The polyols employed can have hydroxyl numbers which vary over a wide range. In general, the hydroxyl numbers of the polyols employed in the invention can range from about 20, and lower, to about 150, and higher. The hydroxyl number is defined as the number of milligrams of potassium hydroxide required for the complete hydrolysis of the fully acetylated derivative prepared from 1 gram of polyol. The hydroxyl number can also be defined by the equation:

$$OH = (56.1 \times 1000 \times f/m.w.)$$

wherein
OH = hydroxyl number of the polyol
f = functionality, that is, average number of hydroxyl groups per molecule of polyol
m.w. = molecular weight of the polyol The exact polyol employed depends upon the end-use of the polyurethane product to be produced. The molecular weight or the hydroxyl number is selected properly to result in flexible or semi-flexible foams when the polyol is converted to a polyurethane. The polyols preferably possess a hydroxyl number of from about 50 to about 150 for semi-flexible foams and from about 30 to about 70 for flexible foams. Such limits are not intended to be restrictive, but are merely illustrative of the large number of possible combinations of the above polyol coreactants.

The organic polyisocyanates that are useful in producing polyurethane foams in accordance with this invention are organic compounds that contain at least two isocyanato groups. Such compounds are well known in the art of producing polyurethane foams. Suitable organic polyisocyanates include the hydrocarbon diisocyantes, (e.g., the alkylene diisocyanates and the arylene diisocyanates) as well as known triisocyanates. As examples of suitable polyisocyanates one can mention 1, 2-diisocyanatoethane, 1, 3-diisocyanatopropane, 1, 2-diisocyanatopropane, 1, 4-diisocyanatobutane, 1, 5-diisocyanatopentane, 1, 6-diisocyanatohexane, bis(3-isocyanatopropyl)ether, bis(3-isocyanatopropyl)sulfide, 1, 7-diisocyanatoheptane, 1, 5-diisocyanato-2, 2-dimethylpentane, 1, 6-diisocyanato-3-methoxyhexane, 1, 8-diisocyanatooctane, 1, 5-diisocyanato-2, 2, 4-trimethylpentane, 1, 9-diisocyanatononane, 1, 10-diisocyanatopropyl)ether of 1, 4-butylene glycol, 1, 11-diisocyanatoundecane, 1, 12-diisocyanatododecane bis(isocyanatohexyl) sulfide, 1, 4-diisocyanatobenzene, 2, 4-diisocyanatotoluene, 2, 6-diisocyanato tolylene, 1, 3-diisocyanato-o-xylene; 1, 3-diisocyanato-m-xylene, 1, 3-diisocyanato-p-xylene, 2, 4-diisocyanato-1-chlorobenzene, 2, 4-diisocyanato-1-nitrobenzene, and 2, 5-diisocyanato-1-nitrobenzene and mixtures thereof.

The catalysts that are useful in producing polyurethane foams in accordance with this invention include: (a) tertiary amines such as bis(dimethylamino ethyl)ether, trimethylamine, triethylamine, N-methylmorpholine, N-ethylmorpholine, N,N-dimethylbenzylamine, N,N-dimethylethanolamine, N,N,N',N'-tetramethyl-1,3-butanediamine, triethanolamine, 1,4-diazabicyclo[2.2.2]octane, pyridine oxide and the like; (b) tertiary phosphines such as trialkylphosphines, dialkylbenzylphosphines, and the like; (c) strong bases such as alkali and alkaline earth metal hydroxides, alkoxides, and phenoxides; (d) acidic metal salts of strong acids such as ferric chloride, stannic chloride, stannous chloride, antimony trichloride, bismuth nitrate and chloride, and the like; (e) chelates of various metals such as those which can be obtained from acetylacetone, benzoylacetone, trifluoroacetylacetone, ethyl acetoacetate, salicylaldehyde, cyclopentanone-2-carboxylate, acetylacetoneimine, bisacetylacetonealkylene-diimines, salicylaldehydeimine, and the like, with various metals such as Be, Mg, Zn, Cd, Pb, Ti, Zr, Sn, As, Bi, Cr, Mo, Mn, Fe, Co, Ni, or such ions as $MoO_2++$, $UO_2++$, and the like; (f) alcoholates and phenolates of various metals such as $Ti(OR)_4$, $Sn(OR)_4$, $Sn(OR)_2$, $Al(OR)_3$, and the like, wherein R is alkyl or aryl, and the reaction products of alcoholates with carboxylic acids, betadiketones, and 2-(N,N-dialkylamino)alkanols, such as the well known chelates of titanium obtained by said or equivalent procedures; (g) salts of organic acids with a variety of metals such as alkali metals, alkaline earth metals, Al, Sn, Pb, Mn, Co, Ni, and Cu, including, for example, sodium acetate, potassium laurate, calcium hexanoate, stannous acetate, stannous octoate, stannous oleate, lead octoate, metallic driers such as manganese and cobalt naphthenate, and the like; (h) organometallic derivatives of tetravalent tin, trivalent and pentavalent As, Sb, and Bi, and metal carbonyls of iron and cobalt.

Among the organotin compounds that deserve particular mention are dialkyltin salts of carboxylic acids, e.g. dibutyltin diacetate, dibutyltin dilaurate, dibutyltin maleate, dilauryltin diacetate, dioctyltin diacetate, dibutyltin-bis(4-methylaminobenzoate), dibutyltin-bis(6-methylaminocaproate), and the like. Similarly there may be used a trialkyltin hydroxide, dialkyltin oxide, dialkyltin dialkoxide, or dialkyltin dichloride. Examples of these compounds include trimethyltin hydroxide, tributyltin hydroxide, trioctyltin hydroxide, dibutyltin oxide, dioctyltin oxide, dilauryltin oxide, dibutyltin-bis-(isopropoxide), dibutyltinbus(2-dimethylaminopentylate), dibutyltin dichloride, dioctyltin dichloride, and the like.

The tertiary amines may be used as primary catalysts for accelerating the reactive hydrogen/isocyanate reaction or as secondary catalysts in combination with one or more of the above noted metal catalysts. Metal catalysts, or combinations of metal catalysts, may also be employed as the accelerating agents, without the use of amines. The catalysts are employed in small amounts, for example, from about 0.001 percent to about 5 percent, based on weight of the reaction mixture.

Foaming is accomplished by employing a small amount of a polyurethane blowing agent, such as water, in the reaction mixture (for example, from about 0.5 to about 5 weight percent of water, based upon total weight of the polymer/polyol composition), or through the use of blowing agents which are vaporized by the exotherm of the reaction, or by a combination of the two methods. Illustrative polyurethane blowing agents include halogenated hydrocarbons such as trichloromonofluoromethane, dichlorodifluoromethane, dichloromonofluoromethane, dichloromethane, trichloromethane, 1,1-dichloro-1-fluoroethane, 1,1,2-trichloro-1,2,2-trifluoromethane, hexafluorocyclobutane, octafluorocyclobutane, and the like. Another class of blowing agents include thermally-unstable compounds which liberate gased upon heating, such as N,N'-dimethyl-N,N'-dinitrosoterephthalamide, and the like. The generally preferred method of foaming for producing flexible foams is the use of water or a combination of water plus a fluorocarbon blowing agent such as trichloromonofluoromethane. The quantity of blowing agent employed will vary with factors such as the density desired in the foamed product. Generally, the use of water in an amount of at least 3.0 percent by weight based on the total weight results in a foam having a density of less than 1.75 pounds per cubic foot.

In producing cellular polyurethanes in accordance with the the method of this invention, a minor amount of an organosilicone or a silicone-free, organic surfactant may also be present as an additional component of the polyurethane-forming reaction mixture, organosilicone surfactants being preferred. When used, such surfactants are usually present in amounts up to about 5 parts by weight per 100 parts by weight of total polyol reactant.

Suitable classes of silicone surfactants are the polysiloxanepolyoxyalkylene block copolymers wherein the respective blocks are joined through silicon-to-carbon or silicon-to-oxygen-to-carbon bonds and the respective polyoxyalkylene blocks are bonded to different silicon atoms of the polysiloxane backbone to form a comb-like structure. Usually, the polysiloxane blocks are trialkylsiloxy-endblocked. In addition to the siloxy units to which the pendant polyoxyalkylene chains are bonded, the polysiloxane backbone is formed of difunctional siloxy units wherein the respective two remaining valences of silicon are satisfied by bonds to organic radicals. Illustrative of such organic radicals are the hydrocarbyl groups having from 1 to 12 carbon atoms including alkyl, aryl, aralkyl, bicycloheptyl and halogen-substituted derivatives of such groups. The polyoxyalkylene blocks are usually constituted of oxyethylene units, oxypropylene units or a combination of such units, and the polyoxyalkylene chains are hydroxyl-terminated or capped with a monovalent organic group such as alkyl, aryl, aralkyl, acyl, carbamyl and the like.

A second type of foam-stabilizing component which can be present in the formulations described herein are the branched block copolymers described in U.S. Pat. No. 2,834,748. Organosilicone foam stabilizers described in the latter patent include those containing a trifunctional siloxy unit to which three polyoxyalkylene blocks are bonded through dialkyl-substituted siloxy units. A preferred group are those having the formula, $MeSi[OSiMe_2)_d(OC_aH_{2a})_bOR]_3$, wherein Me is methyl, d has a value of at least one, a is from 2 to 3, b has a value of at least 5, and R is hydrogen or a monovalent hydrocarbyl group such as lower alkyl, butyl being especially suitable.

Other useful foam-stabilizing components are block copolymers wherein the polysiloxane blocks are trialkylsiloxy-endblocked and contain recurring difunctional dialkylsiloxy monomeric units in combination with reoccurring difunctional cyanoalkyl-alkylsiloxy or cyanoalkoxy-alkylsiloxy monomeric units, the mole ratio of the dialkylsiloxy units to the cyano-substituted siloxy units being about 10–200:3–100, and wherein the polysiloxane and polyoxyalkylene blocks are joined through an Si-C or an Si-O-O linkage, and from about 20 to about 65 weight percent of the oxyalkylene content of the polyoxyalkylene blocks is constituted of oxyethylene units. These block copolymers are described and claimed in copending application Ser. No. 279,883, filed Aug. 11, 1972, in the names of Bela Prokai and Bernard Kanner. A preferred class of such surfactants are the cyanopropyl-substituted block copolymers having the average formula,

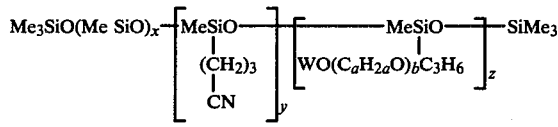

wherein: Me represents methyl; W represents a monovalent hydrocarbyl group ($R'$-), an acyl group [$R'C(O)$-] or a carbamyl group [$R'NHC(O)$-], the said $R'$ group having from 1 to 12 carbon atoms; x has an average value of from about 20 to about 100; y has an average value of from about 4 to about 30; z has an average value of from about 2 to about 10; a has a value of from 2 to 4, provided from about 20 to about 65 weight percent of the oxyalkylene units of the polyoxyalkylene chain, —$(C_aH_{2a}O)_b$—, are constituted of oxyethylene; and b has an average value such that the average molecular weight of the polyoxyalkylene chain is from about 1000 to about 6000.

Still further suitable silicon-containing foam stabilizers include the polysiloxane-polyoxyalkylene block copolymers described, for example, in U.S. Pat. No. 3,563,924 and 3,594,334. Such copolymers include those characterized by a particular molecular weight (600–17000), siloxane content (14–40 weight percent based on the weight of the copolymer) and oxyethylene content (at least 75 weight percent based on the total amount of oxyalkylene groups in the copolymer). The organosilicones are usually employed in combination with an anionic, silicon-free organic emulsifier such as those described in said U.S. Pat. No. 3,594,334, the teachings of which are incorporated herein by reference. Also effective as stabilizers are the organoslicones containing tetrafunctional $SiO_{4/2}$ units described and claimed in copending application Ser. No. 132,534, filed Apr. 8, 1971, in the names of Bela Prokai and Bernard Kanner. Of this class of stabilizers, those having the following average formula are particularly preferred:

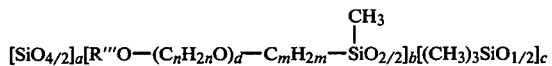

wherein n has a value of 2 to 4 inclusive; d has an average value of from about 5 to about 15; m has a value of from 2 to 4; a:b:c has an average value of 0.4–2:1:0.2–2, and $R'''$ is phenyl, lower alkyl, lower alkaryl or arylsubstituted lower alkyl groups. Particularly effective are polymers in which at least a major proportion of the poly (oxyalkylene) chains are terminated by $R°°°O$— groups where the organic cap ($R°°°$) is methyl or benzyl.

Still further useful silicone surfactants include cyanopropylsubstituted polymethylsiloxane-polyoxyethylene copolymers described in copending application Ser. No. 457,510, filed Apr. 3, 1974, of Bela Prokai and Bernard Kanner. Other useful silicone surfactants comprise the cyanoalkoxyalkyl-modified polyalkylsiloxane-polyoxyethylene copolymers described in copending application Ser. No. 536,884, filed Dec. 27, 1974, of Bela Prokai and Bernard Kanner.

Silicon-free, organic surfactants or emulsifiers suitable as stabilizers of the polyester polyol-based urethane foams described herein are known to the art and are employed in amounts up to about 5 p.p.h.p. One class of organic emulsifiers suitable for this purpose are products obtained by the reaction of amines such as, in particular, diethylamine, with long chain fatty acids such as oleic acid or with sulfonated $C_{10}$–$C_{15}$ alkylated aromatic hydrocarbons. Another class are the liquid, anionic organic surfactants having at least one carbon-bonded sulfonic acid group, —$SO_3H$, or an ammonium, quaternary ammonium, alkali metal or alkaline earth metal derivative of said sulfonic acid group. The sulfonic acid groups or salt derivatives thereof can be substituents on a wide variety of "backbone" organic compounds which provide the hydrophobic portion of the emulsifier.

The hydrophobic portion may consist of carbon and hydrogen as in sulfonated hydrocarbons (or salt derivatives thereof) having from 10 to 20 or more carbon atoms such as alkanes, high alkyl-substituted benzenes, and liquid petroleum fractions, as typically illustrated by sodium tetradecyl sulfonate, sodium dodecylbenzene sulfonate and sodium and potassium salts of sulfonated mineral oil. The —$SO_3H$ group or salt derivative thereof may also be a substituent on an organic backbone consisting of carbon, hydrogen and oxygen wherein oxygen is present in an ether linkage as in polyoxyalkylene groups or in a carboxylic acid ester group. Typical of such compounds are those obtained by sulfating or sulfonating oxyalkylated fatty acid esters wherein the oxyalkylation is usually effected with ethylene oxide, propylene oxide or a combination thereof. These and other organic stabilizers of polyester polyol-derived urethane foams are known to the art; see, for example, the description thereof in U.S. Pat. No. 3,594,334.

If desired, other additional ingredients can be employed in minor amounts in producing the polyurethane foams in accordance with the process of this invention. Illustrative of such additives that can be employed are: compression set additives (e.g., hexylene glycol); additives to regulate cell structure so as to coarsen cells and thereby reduce the tendency of the foam to split (e.g., paraffin oil); fillers; dyes; pigments; anti-discoloration additives including anti-scorch and anti-oxidation agents; and the like.

The novel haloroalkyl polyphosphates of the present invention may be compounded with the foam formulation by any of the techniques conventionally used for flame retardant additives. The amount which should be used can be varied within wide limits. As little as about 5 to 7 parts per 100 parts by weight of the polyol provide the resulting flexible foams with satisfactory flame retardancy.

The following Examples are illustrative, but not in limitation, or the present invention.

DEFINITIONS

As used in the Examples appearing hereinafter, the following designations, symbols, terms and abbreviations have indicated meanings:

| TERMS | DEFINITIONS |
|---|---|
| Polyol A | A propoxylated/ethoxylated polyol having a hydroxyl number of 47 mg. KOH/gm. and a functionality of 3. |
| Polyol B | A polypropylene oxide triol produced from propylene oxide and glycerine and having a molecular weight of about 3,000. |
| Polyol C | A propoxylated/ethoxylated polyol having a hydroxyl number of about 56 mg. KOH/gm. |
| Surfactant | A silicone surfactant having the structure: $Me_3SiO(Me_2SiO)_{60}(MeSi\ polyether)_6NCC_3H_6SiMeO)_{10}SiMe_3$ wherein the polyether = $C_3H_6O(C_2H_4O)_{24}(C_3H_6O)_{27}Me$ |
| TDI | A mixture of about 80 weight percent 2,4-tolylene diisocyanate and about 20 percent 2,6-tolylene diisocyanate. |
| Flame Retardant A | Thermal condensate of tris(2-chloroethyl)phosphate (Stauffer Chemical Company, "Fyrol 99"). |
| Flame Retardant B | $(ClCH_2)_2C[CH_2OP(OCH_2CH_2Cl)_2]_2$ (Monsanto Chemical Company, "Phosgard 2XC-20"). |
| Flame Retardant C | A polymeric chloroethylphosphate (Olin Corp., "Thermolin 101"). |
| Flame Retardant D | Tris(2,3-dibromopropyl) phosphate (Michigan Chemical Company, "T 23 P"). |
| Flame Retardant E | Brominated castor oil (Swift Chemical Company, "Brominex$^R$ 257"). |
| Flame Retardant F | Chlorinated phosphonate ester (Mobil Chemical Company, "Antiblaze$^R$ 78"). |
| Flame Retardant G | Pentabromylbiphenyl oxide. |
| Flame Retardant H | A mixture of tris (2,3-dichloropropyl) phosphate and tris (1,3-dichloropropyl) phosphate (Stauffer Chemical Company, "Fyrol FR2"). |
| Gel Time | The observed elapse of time from the time the foaming mixture was poured into a container and stringing (gelation) of the polymer occurs as determined by intermittently protruding the top of the foam with a spatula. |
| California Vertical Flame Test | "Technical Information Bulletin Number 117", State of California Dept. of Consumer Affairs, Bureau of Home Furnishings, Sacramento, California, May 1974. |
| CT | Cream Time - The interval of time from the formation of the complete foam formulation to the appearance of a creamy color in the formulation. The creaming time is proportional to the rate of reaction of the formulation. |
| RT | Rise Time - The interval of time from the formation of the complete foam formulation to the attainment of the maximum height of the foam. |
| Porosity | A specimen of foam ½ inch in thickness is compressed between two pieces of flanged plastic tubing 2¼ inches in diameter (ID). This assembly then becomes a component in an air flow system. Air at a controlled velocity enters one end of the tubing, flow through the foam specimen and exits through a restriction at the lower end of the assembly. The pressure drop across the foam due to the restriction of air passage is measured by means of an inclined closed manometer. One end of the manometer is connected to the upstream side of the foam and the other end to the downstream side. The flow of air on the upstream side is adjusted to maintain a differential pressure across the specimen of 0.1 inch of water. The air porosity of the foam is reported in units of air flow per unit area of specimen, cubic feet per minute per square foot. |
| Tensile Strength | ASTM D1564-69 |
| Tear Resistance | ASTM D1564-69 |
| ILD | ASTM D1564-69 |
| Return Value | ASTM D1564-69 |
| Load Ratio | ASTM D1564-69 |
| Compression Set | ASTM D1564-69 |
| Burning Extent, Extinguishing Time, Burning Rate | Determined by ASTM D1692-67T (modified to the extent that 5 foam specimens are used rather than 10) as follows: The flame of a Bunsen burner having an inner blue cone of about 1.5 inches in height is applied separately to the front edges of five foam specimens. The dimensions of the specimens are 6" × 2" × 0.5". The flame is allowed to remain in contact with the specimens for about sixty seconds. The extent of burning (Burning Extent) of the foam is |

| TERMS | DEFINITIONS |
|---|---|
| | the average distance from the front edge of the specimens to the furthermost point on the specimens reached by the flame front. A foam is rated self-extinguishing (SE) when each of the five specimens has a Burning Extent of less than five inches. If the Burning Extent of one or more of the specimens is at least five inches, the foam is rate Burning. The average time interval from the application of the flame to the specimens to the cessation of burning (due to total consumption of the specimen or to the flame dying out) is the Extinguishing Time of the foam. The Burning Rate of a foam is its Burning Extent divided by its Extinguishing Time. |
| Dry Heat Aging | The foam sample was heated in an oven at 140° C. for 22 hours, as specified in ASTM D-1564-64T, Sections 36–44. |
| Humid Aging | The foam sample was subjected to heating at 120° C. for 5 hours in a steam autoclave, as specified in ASTM D-1564-64T, Section 5.1.2. |

EXAMPLES 1-2

These Examples illustrate the formation of novel organophosphates in accordance with the present invention utilizing as the reactants, tris(2-chloroethyl) phosphate and triethylphosphate. In Example 2, the relative molar amount of the triethylphosphate was significantly increased.

The mixture of the two reactants together with anhydrous sodium carbonate catalyst were placed in a No. 1—liter, No. 4—necked flask equipped with a Trubor stirrer, thermometer, Claisen distillation head and a nitrogen inlet tube. A means was provided to pass the exit gases through two cold traps immersed in series in a mixture of dry ice and acetone. The flask was heated by means of a heating mantle.

For Example 1, the following time-temperature profile was logged:

| Time, min. | Kettle Temp., °C. | Vapor Temp., °C. | Total Distillate Collected, gms. |
|---|---|---|---|
| 0 | 28 | 24 | — |
| 15 | 110 | 24 | — |
| 30 | 150 | 24 | — |
| 60 | 168 | 30 | Distillation commenced |
| 75 | 167 | 41 | — |
| 90 | 170 | 50 | 6.00 |
| 105 | 170 | 57 | 14.20 |
| 145 | 166 | 52 | 26.20 |
| 215 | 174 | 58 | 49.60 |
| 250 | 178 | 60 | 66.30 |

Neutralization of the acid was effected by heating the residue with 10 grams of epichlorohydrin for 1 hour at 100° C. in Example 1 and by treatment with propylene oxide in Example 2. The product was refined by passing the crude material through a Rota-Film Molecular Still maintained at a jacket temperature of 100° C. and 0.2 mm. Hg. pressure. Analysis of the cold trap gases was performed by mass spectrometry.

The original distillate from the Rota-Film Molecular Still was analyzed by vapor phase chromatography-mass spectrometry to determine the relative amounts of 1,2-dichloroethane and chloroethane. The contents of the cold traps were expanded into a gas tube; and, by the use of mass spectrometry, the contents were determined to be entirely chloroethane.

The results are set forth in Table I:

TABLE I

| Example | 1 | 2 |
|---|---|---|
| Charge Composition | | |
| Tris (2-chloroethyl) Phosphate, gms. (moles) | 299.8 (1.05) | 285.5 (1.00) |
| Triethylphosphate, gms. (moles) | 182.2 (1.00) | 547.0 (3.00) |
| Sodium Carbonate, gms. | 1.5 | 1.5 |
| Conditions | | |
| Temperature, °C. | 168–178 | 162–178 |
| Pressure, mm. Hg. | 760 | 760 |
| Acid Number of residue product, mg KOH/g. | 6.22 | 3.90 |
| Neutralized Residue[a] | Epichlorohydrin | Propylene Oxide |
| Yield, gms. | 296 | 365 |
| Acid Number, mg KOH/gm. | nil | 1.44 |
| Viscosity, cps. at 25° C. | 480 | — |
| Gardner Color | 2.0 | — |
| Phosphorus, % | 18.25 | 17.11 |
| Chloride, % | 16.28 | 8.70 |
| Carbon, % | 28.49 | 30.93 |
| Hydrogen, % | 5.37 | 6.08 |
| Cold Traps from Refining Neutralized Product[a] | | |
| 1,2-Dichloroethane | 0 | 14.9 |
| Chloroethane | 53.4 | 53.1 |
| Vinyl Chloride | 2.2 | 0 |
| Distillate Collected (original) | | |
| Yield, gms. | 66 | 36.8 |

TABLE I-continued

| Example | 1 | 2 |
|---|---|---|
| Composition | | |
| 1,2-Dichloroethane, gms. (%) | 41.58 (63) | 20.24 (55) |
| Chloroethane, gms. (%) | 23.1 (35) | 16.56 (45) |
| Cold Traps | | |
| Yield, gms. | 10 | 47.4 |
| Chloroethane, % | 100 | 100 |
| Total 1,2-Dichloroethane, moles | 0.420 | 0.355 |
| Total Chloroethane, moles | 1.34 | 1.815 |

[a] During refining the excess triethylphosphate in Example 2 was recovered. The cold traps contained 255.7 g. and the distillate totaled 120.9 g. amounting to 2.06 moles recovered triethylphosphate. In Example 1, only 7.4 g. of triethylphosphate was recovered in the distillate.

As can be seen, the increase of the relative amount of triethylphosphate in Example 2 significantly increased the molar ratio of chloroethane to 1, 2-dichloroethane.

EXAMPLES 3–7

These Examples illustrate the use of the novel organophosphates of the present invention in connection with a flexible urethane foam formulation in contrast to a control and a commercially available flame retardant.

The organophosphate used was the product formed in Example 1 and the foam formulation (except for the catalysts) was as follows, the parts being by weight:

| Polyol A | 100 parts |
|---|---|
| Water | 4.0 parts |
| Surfactant | 1 part |
| TDI | 48 |
| TDI Index | 105 |

The results are set forth in Table II:

TABLE II

| Example | 3 | 4 | 5 | 6 | 7 |
|---|---|---|---|---|---|
| Amine Catalyst* | 0.125 | 0.125 | 0.125 | 0.125 | 0.200 |
| Stannous Octoate | 0.225 | 0.225 | 0.225 | 0.250 | 0.300 |
| Flame Retardant A | 10 | — | — | — | — |
| Organo phosphate | 0 | 0 | 5 | — | — |
| CT/RT, sec. | 6/97 | 8/85 | 6/84 | 8/98 | 5/79 |
| Density, pcf. | 1.73 | 1.61 | 1.62 | 1.74 | 1.47 |
| Porosity, ft$^3$/min./ft$^2$ | 47 | 15 | — | 0 | 9 |
| Tensile Strength, psi | 14.1 | 17.6 | — | 11.3 | 10.7 |
| Elongation, % | 212 | 207 | — | 175 | 192 |
| Tear Resistance, lbs./in. | 2.21 | 2.53 | — | 1.97 | 1.98 |
| Resiliency, % ball rebound | 43 | 50 | 50 | 50 | 50 |
| 4-Inch ILD lbs./50 in.$^2$ | | | | | |
| 25% deflection | 33 | 42 | 33 | 34 | 34 |
| 65% deflection | 64 | 73 | 63 | 63 | 60 |
| 25% deflection | 22 | 27 | 26 | 23 | 22 |
| Return Value | 67.5 | 64 | 79 | 66 | 65 |
| Load Ratio | 1.96 | 1.74 | 1.93 | 1.83 | 1.79 |
| 90% Compression Set, % | 7.6 | 4.5 | — | 4.1 | 9.8 |
| Flammability | | | | | |
| Oxygen Index | — | 15.96 | 21.26 | 23.66 | 23.66 |
| Burning Extent, inches | 1.9 | — | 1.9 | 1.1 | 1.0 |
| Extinguishing Time, sec. | 27 | — | 31 | 21 | 19 |
| Burning Rate, in./min. | 4.02 | 6.13 | 3.51 | 3.03 | 2.89 |
| After Dry Heat Aging: | | | | | |
| Burning Extent, inches | >5 | >5 | 2.2 | 1.4 | 1.1 |
| Extinguishing Time, sec. | — | — | 31 | 18 | 19 |
| Burning Rate, in./min. | 5.02 | 5.74 | 4.14 | 4.44 | 3.13 |
| After Humid Aging: | | | | | |
| Burning Extent, inches | 1.6 | — | 2.4 | 1.1 | 1.1 |
| Extinguishing Time, sec. | 23 | — | 36 | 20 | 19 |
| Burning Rate, in./min. | 4.08 | 5.53 | 4.06 | 3.03 | 3.33 |

*Commercially available and principally used for forming flexible urethane foams.

As can be seen, as low as 5 parts of the novel organophosphates of the present invention imparted durable fire resistance while the control sample and the samples including the commercially available flame retardant (10 parts) failed after Dry Heat Aging.

It should be noted that the control may well not show optimum properties inasmuch as it was subsequently found that a defective batch of catalyst had been used.

EXAMPLE 8

Using the procedure described in Examples 1–2, further samples of the chloroalkylphosphates of the present invention were made from the following charge:

| Component | Weight, gms., (moles) |
|---|---|
| Tris (2-chloroethyl)phosphate* | 599.54 (2.10) |
| Triethylphosphate | 364.32 (2.00) |
| Sodium carbonate catalyst | 3.0 |

*Dried over molecular sieves.

The time-temperature profile logged was as follows:

| Time, min. | Kettle Temp., °C. | Vapor Temp., °C. | Total Distillate Collected, gms. |
|---|---|---|---|
| 0 | 24 | 24 | — |
| 8 | 68 | 24 | — |
| 38 | 144 | 24 | — |
| 63 | 164 | 33 | — |
| 83 | 171 | 41 | — |
| 113 | 171 | 59 | 20.9 |
| 173 | 171 | 64 | 61.1 |
| 218 | 173 | 63 | 97.3 |
| 233 | 173 | 59 | 109.2 |

The residue had an acid number of 6.58, and the distillate (by vapor phase chromatography) consisted of 38.09% chloroethane and 61.9% dichloroethane.

Neutralization was effected by treating with 20 cc. of epichlorohydrin in a Rota-Film Molecular Still at 100° C. for 2 hours and 10 minutes with a high vacuum (the pressure being 0.25 mm. Hg.), the following being collected: cold traps—181 grams; distillate—65 grams and residue—578 grams. The acid number of the thus-treated residue was 2.73 mg. KOH/gm.

A further neutralization was effected by treating with 10 cc. epichlorohydrin at 100° C. for 1 hour. The resulting residue (532 grams) had the following properties: Acid number—0.174 mg. KOH/gm., Viscosity (25° C.)—332.5 cps. and Color (Gardner)—2.0.

EXAMPLES 9–45

Samples of the organophosphate residue of Example 8 (acid number—0.174 mg. KOH/gm.) were added to a polyether foam formulation in varying amounts using two different surfactants, and the flammability characteristics and foam properties were compared with foams formed using other commercially available flame retardants.

The foam formulation, in parts by weight, is as follows:

| Formulation | Parts By Weight |
|---|---|
| Polyol B | 100.0 |
| Water | 3.8 |
| Amine Catalyst* | 0.1 |
| Surfactant | 0.1 |
| Stannous octoate | 0.3 |
| TDI | 105 Index |

The physical properties of the resulting bench mixed, free rise flexible foams and their combustibility properties together with the amounts of the various flame retardants employed are set forth in Table III below:

TABLE III

| EXAMPLE | 9 | 10 | 11 | 12 | 13 | 14 | 15 | 16 | 17[a] | 18[a] |
|---|---|---|---|---|---|---|---|---|---|---|
| Additive, parts by weight | | | | | | | | | | |
| Example 8 product | 2.5 | 3.0 | 3.5 | — | — | — | — | — | — | — |
| Flame retardant B | — | — | — | — | 2.0 | 4.0 | 6.0 | — | — | — |
| Flame retardant C | — | — | — | — | — | — | — | 2.0 | 4.0 | 6.0 |
| Physical Properties | | | | | | | | | | |
| Density, lbs/ft$^3$ | 1.64 | 1.67 | 1.67 | 1.65 | 1.63 | 1.64 | 1.68 | 1.66 | 1.65 | 1.67 |
| Porosity, ft$^3$/min/ft$^2$ | 86.6 | 85.0 | 84.5 | 73.6 | 68.3 | 72.0 | 72.0 | 79.0 | 70.0 | 84.0 |
| 65% ILD, lbs. | 63.5 | 63.2 | 63.2 | 64.8 | 59.8 | 57.0 | 57.1 | 60.4 | 58.0 | 54.7 |
| Load Ratio | 1.84 | 1.84 | 1.81 | 1.83 | 1.80 | 1.85 | 1.77 | 1.86 | 1.80 | 1.86 |
| Tear Resistance, lbs/in. | NA[b] | NA | NA | 2.65 | 2.71 | 2.87 | 2.67 | 2.66 | 2.61 | 2.56 |
| Combustibility Properties | | | | | | | | | | |
| California Vertical Flame Test, Avg. Char Length, inches, | 3.81 (1>12.0)[c] | 2.34 | 2.17 | >12.0 | (2>12.0)[d] | 2.38 | 2.46 | 4.30 | 2.68 | 3.24 |

[a]Examples 17 and 18 were made with 0.35 parts by weight stannous octoate and 0.2, 0.3 parts by weight amine catalyst, respectively.
[b]NA = not available.
[c],[d]1 and 2 specimens, respectively, of the specimens tested had a char length of greater than 12 inches.

| EXAMPLE | 19 | 20 | 21 | 22 | 23 | 24 | 25 | 26 | 27 | 28 | 29 |
|---|---|---|---|---|---|---|---|---|---|---|---|
| Additive, parts by weight | | | | | | | | | | | |
| Flame retardant D | — | 2.0 | 4.0 | 6.0 | — | — | — | 1.0 | 2.0 | — | — |
| Flame retardant E | — | — | — | — | 2.0 | 4.0 | 6.0 | — | — | — | — |
| Flame retardant F | — | — | — | — | — | — | — | 2.0 | 4.0 | 3.0 | 6.0 |
| Physical Properties | | | | | | | | | | | |
| Density, lbs/ft$^3$ | 1.64 | 1.66 | 1.68 | 1.70 | 1.69 | 1.68 | 1.67 | 1.64 | 1.68 | 1.66 | 1.68 |
| Porosity, ft$^3$/min/ft$^2$ | 61.0 | 67.5 | 67.5 | 64.0 | 51.5 | 55.5 | 55.5 | 79.6 | 74.1 | 73.1 | 86.0 |
| 65% ILD, lbs. | 59.2 | 60.4 | 59.2 | 65.6 | 70.0 | 65.9 | 62.2 | 59.9 | 61.2 | 63.0 | 56.3 |
| Load Ratio | 1.83 | 1.74 | 1.73 | 1.76 | 1.75 | 1.79 | 1.78 | 1.78 | 1.79 | 1.81 | 1.76 |
| Tear Resistance, lbs/in. | 1.81 | 2.63 | 2.82 | 2.87 | 3.10 | 2.79 | 2.78 | 2.74 | 2.53 | 2.48 | 2.42 |
| Combustibility Properties | | | | | | | | | | | |
| California Vertical Flame Test, Avg. Char Length, inches, | >12.0 | 3.50 | 2.04 | 2.24 | 2.74 | 2.26 | 1.88 | 2.44 | 2.20 | 3.30 | 2.34 |

| EXAMPLE | 30 | 31 | 32 | 33 | 34 | 35 |
|---|---|---|---|---|---|---|
| Additive, parts by weight | | | | | | |
| Flame retardant D | 0.5 | — | — | — | — | — |
| Flame retardant E | 1.0 | 1.5 | 1.0 | 2.0 | 2.0 | 2.5 |
| Flame retardant F | — | — | 0.5 | 1.0 | — | — |
| Physical Properties | | | | | | |
| Density, lbs/ft$^3$ | 1.67 | 1.68 | 1.67 | 1.71 | 1.67 | 1.68 |
| Porosity, ft$^3$/min/ft$^2$ | 77.5 | 75 | 78.5 | 87 | 78.5 | 82 |
| 65% ILD, lbs. | 60.4 | 61.3 | 60.2 | 59.2 | 61.6 | 61.8 |
| Load Ratio | 1.78 | 1.77 | 1.73 | 1.83 | 1.77 | 1.72 |
| Tear Resistance, lbs/in. | 2.73 | 2.82 | 2.97 | 2.82 | 2.58 | 2.53 |
| Combustibility Properties | | | | | | |
| California Vertical Flame Test, Avg. Char Length, inches, | 4.60 (1>12.0)[a] | 4.30 (1>12.0)[a] | 3.49 | 2.62 | 2.59 | 2.24 |

[a]1 of the specimens tested had a char length greater than 12 inches.

| EXAMPLE | 36 | 37 | 38 | 39 | 40 | 41 | 42 | 43 | 44 | 45 |
|---|---|---|---|---|---|---|---|---|---|---|
| Additive, parts by weight | | | | | | | | | | |
| Flame retardant G | 1.0 | 0.5 | 2.0 | 3.0 | 5.0 | 0.5 | 0.5 | 1.0 | — | — |
| Flame retardant E | 2.0 | 1.0 | — | — | — | — | 0.5 | — | 1.0 | 2.0 |
| Flame retardant B | — | — | — | — | — | 1.0 | 0.5 | 2.0 | 2.0 | 1.0 |
| Physical Properties | | | | | | | | | | |
| Density, lbs/ft$^3$ | 1.72 | 1.69 | 1.66 | 1.71 | 1.72 | 1.68 | 1.69 | 1.70 | 1.73 | 1.72 |
| Porosity, ft$^3$/min/ft$^2$ | 79 | 79 | 78 | 75.7 | 77 | 73.6 | 73.1 | 78.5 | 71.6 | 73.6 |
| 65% ILD, lbs. | 60.9 | 70.3 | 70.2 | 72.2 | 70.8 | 72.1 | 71.5 | 69.9 | 70.4 | 71.8 |
| Load Ratio | 1.81 | 1.83 | 1.91 | 1.89 | 1.88 | 1.86 | 1.86 | 1.86 | 1.90 | 1.89 |
| Tear Resistance, lbs/in. | 2.60 | 2.47 | 2.51 | 2.42 | 2.50 | 2.47 | 2.41 | 2.52 | 2.69 | 2.41 |
| Combustibility Properties | | | | | | | | | | |
| California Vertical Flame | | | | | | | | | | |

TABLE III-continued

| Test, Avg. Char Length, inches, | 3.59 | >12.0 | >12.0 | >12.0 | 2>12.0[a] | 8.58 | 2>12.0[a] | 3.05 | 2.61 | 2.69 |
|---|---|---|---|---|---|---|---|---|---|---|

[a] 2 of the specimens tested had a char length greater than 12 inches.

As can be seen, with both surfactants, significant improvement in the combustibility properties is achieved in comparison to the control of Example 12 with the inclusion of relatively minor amounts of the organophosphates of the present invention.

EXAMPLE 46

To further demonstrate the process of the present invention, a larger scale run was made using a jacketed autoclave having a maximum operating volume of 13.8 gallons and equipped with a 9-inch diameter, 3-blade turbine for agitation. The charge was as follows:
Triethyl phosphate—40 lbs.
Tris(2-chloroethyl)phosphate—66 lbs.
Sodium carbonate catalyst—0.33 lbs.
The reaction conditions were as follows:
Time—3 hrs.
Temperature—175° C.
Pressure—atmospheric
Agitation—48 r.p.m.

Neutralization was effected by treating the reaction product residue with 2.59 lbs. epichlorohydrin for 2 hrs. at 100° C. and atmospheric pressure. The agitation of the autoclave was again 48 r.p.m. Stripping was then carried out under the following conditions:
Time—13.5 hrs.
Temperature—100°–125° C.
Pressure—2 mm. Hg. absolute
Agitation—48 r.p.m.

The stripped residue constituted 63.3 lbs., and 13.3 lbs. of unreacted triethyl phosphate was collected. In addition, in the original condensation, 18.4 lbs. of overhead make was collected (analyzed as 18.6% ethylchloride and 81.35% dichloroethane). The neutralized and stripped residue had the following properties:

| | |
|---|---|
| Viscosity (25° C.) | 16,500 cps. |
| Color (Pt-Co) | 150 |
| Acid Number | 0.137 |
| Analysis, % | |
| Carbon | 28.26 |
| Phosphorus | 17.55* |
| Chlorine | 11.73* |
| Hydrogen | 5.09 |

*Average of two samples.

EXAMPLES 47–59

Samples of the neutralized and stripped residue of Example 46 were used in varying amounts to make hand foams which were compared to foams incorporating other flame retardants. The foam formulations, bench mix data, foam physical and combustibility properties are set forth in Table IV:

TABLE IV

| Example | 47 | 48 | 49 | 50 | 51 | 52 | 53 | 54 | 55 | 56 | 57 | 58 | 59 |
|---|---|---|---|---|---|---|---|---|---|---|---|---|---|
| Foam Formulation, parts by weight | | | | | | | | | | | | | |
| Polyol C | 100 | → | | | | | | | | | | | |
| Water | 4.0 | | | | | | | | | | | | |
| Amine Catalyst | 0.15 | | | | | | | | | | | | |
| Surfactant | 1.0 | | | | | | | | | | | | |
| Stannous octoate | 0.25 | | | | | | | | | | | | |
| TDI | 51.22 | | | | | | | | | | | | |
| Index | 108 | | | | | | | | | | | | |
| Flame Retardant D | — | 3 | 6 | 9 | 12 | — | — | — | — | — | — | — | — |
| Example 45 Residue | — | — | — | — | — | 3 | 6 | 9 | 12 | 3 | 6 | 9 | 12 |
| Flame Retardant H | — | — | — | — | — | — | — | — | — | — | — | — | — |
| Bench Mix Data | | | | | | | | | | | | | |
| Polyol Temperature, F. | 72 | 72 | 72 | 72 | 72 | 72 | 72 | 73 | 73 | 73 | 73 | 73 | 73 |
| Cream Time, Seconds | 8 | 8 | 8 | 8 | 8 | 8 | 8 | 9 | 8 | 8 | 8 | 8 | 8 |
| Rise Time, Seconds | 85 | 88 | 84 | 87 | 91 | 95 | 100 | 103 | 119 | 95 | 96 | 103 | 115 |
| Gel Time, Seconds | 99 | 97 | 99 | 99 | 103 | 105 | 108 | 113 | 132 | 108 | 106 | 115 | 129 |
| Foam Properties | | | | | | | | | | | | | |
| Density | 1.60 | 1.66 | 1.64 | 1.69 | 1.75 | 1.64 | 1.66 | 1.64 | 1.66 | 1.66 | 1.70 | 1.74 | 1.77 |
| Porosity | 51.6 | 50.6 | 48.8(a) | 52.2 | 50.6 | 32.4 | 21.4 | 15.6 | 2.92 | 75.4 | 83.9 | 89.9 | 101 |
| Flammability Rating | B(b) | B | SE | SE | SE(c) | SE | SE | SE | SE | B | B | B | B |
| Burning Extent, in. | — | — | 2.0 | 1.5 | 1.4 | 3.1 | 1.7 | 1.5 | 1.2 | — | — | — | — |
| Extinguishing Time, sec. | — | — | 25 | 21 | 20 | 43 | 22 | 34 | 19 | — | — | — | — |
| Burning Rate, in./min. | — | — | 4.55 | 4.20 | 3.91 | 4.41 | 4.46 | 3.69 | 3.75 | — | — | — | 5.46 |
| California Vertical Flame Test, Average Char Length, in. | >12.0 | 2,11/16 | 2,3/16 | 2,1/2 | 2,5/16 | 4,15/16 | 2,3/4 | 2,3/8 | 1,15/16 | >12.0 | >12.0 | >12.0 | >12.0 |

(a)Light scorch
(b)B = Burning
(c)SE = Self extinguishing

What is claimed is:

1. A method for producing a flexible polyurethane foam which comprises reacting and foaming a reaction mixture containing: (a) an organic polyisocyanate; (b) a polyol; (c) a catalyst for the reaction of (a) and (b); (d) a blowing agent; and (e) a polyphosphate thermal condensate comprising the reaction product of an unsubstituted trialkylphosphate having the following structure:

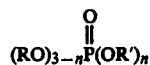

wherein R is $CH_3$, $C_2H_5$, $C_3H_7$ or $C_4H_9$; R' is a $C_5$ to $C_{10}$ hydrocarbon chain and n is 0, 1 or 2 with a 2-haloalkyl phosphate having the following structure:

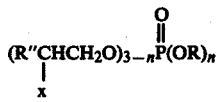

wherein x is Cl or Br; R" is H, $CH_3$, $CH_2Cl$ or $CH_2Br$; and R and n are defined above, said thermal condensate being present in an amount sufficient to impart flame retardancy to the resulting flexible polyurethane foam.

2. The method of claim 1 wherein the mole ratio of the unsubstituted trialkyl phosphate to the 2-haloalkyl phosphate is from about 1:1 to about 2:1.

3. The method of claim 1 wherein the unsubstituted trialkyl phosphate is trimethyl phosphate.

4. The method of claim 1 wherein the unsubstituted trialkyl phosphate is triethyl phosphate.

5. The method of claim 1 wherein the 2-haloalkyl phosphate is a tris (2-haloalkyl) phosphate.

6. The method of claim 1 wherein the tris (2-haloalkyl) phosphate is tris (2-chlorethyl) phosphate.

7. The method of claim 1 wherein the 2-haloalkyl phosphate is a mixture of

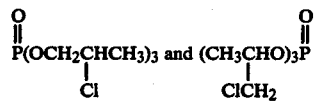

8. The method of claim 1 wherein said thermal condensates are soluble in said polyol.

9. The method of claim 1 wherein said thermal condensates are present in an amount of less than about 7 parts by weight per 100 parts of said polyol.

10. A flexible, flame retarded polyurethane foam produced by the process of claim 1.

* * * * *

UNITED STATES PATENT AND TRADEMARK OFFICE
CERTIFICATE OF CORRECTION

PATENT NO. : 4,162,353
DATED : July 24, 1979
INVENTOR(S) : Papa et al.

It is certified that error appears in the above-identified patent and that said Letters Patent are hereby corrected as shown below:

In column 20, near the top, just under the "Formulation" table, read the footnote --*Commercially available and principally used for forming flexible urethane foams.--.

Signed and Sealed this

Twenty-third Day of October 1979

[SEAL]

Attest:

RUTH C. MASON
Attesting Officer

LUTRELLE F. PARKER
Acting Commissioner of Patents and Trademarks